United States Patent
Ghosh et al.

(10) Patent No.: US 12,136,215 B2
(45) Date of Patent: Nov. 5, 2024

(54) DENTAL IMPLANT RECONSTRUCTION AND RESTORATION BASED ON DIGITAL TWIN

(71) Applicant: INTERNATIONAL BUSINESS MACHINES CORPORATION, Armonk, NY (US)

(72) Inventors: Partho Ghosh, Kolkata (IN); Uri Kartoun, Cambridge, MA (US); Lakshmi Soumya Suggala, Visakhapatnam (IN); Raghu Bhavaraju, Visakhapatnam (IN)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 537 days.

(21) Appl. No.: 17/447,000

(22) Filed: Sep. 7, 2021

(65) Prior Publication Data
US 2023/0074164 A1    Mar. 9, 2023

(51) Int. Cl.
*G06T 7/00* (2017.01)
*A61C 13/00* (2006.01)

(52) U.S. Cl.
CPC ........ *G06T 7/0014* (2013.01); *A61C 13/0004* (2013.01); *G06T 2207/20081* (2013.01);
(Continued)

(58) Field of Classification Search
CPC ......... G06T 7/0014; G06T 2207/20081; G06T 2207/20084; G06T 2207/30036; G06T 2207/30052; A61C 13/0004
See application file for complete search history.

(56) References Cited

U.S. PATENT DOCUMENTS

| 8,348,669 B1 | 1/2013 | Schmitt |
| 8,543,234 B2 * | 9/2013 | Gao ................. B33Y 50/00 700/97 |

(Continued)

FOREIGN PATENT DOCUMENTS

EP    3797732 A1    3/2021

OTHER PUBLICATIONS

Irandoust, et al., "Computer Simulation of Dental implant Treatments," Biomedical Engineering Conference (NEBEC) [conference paper], Apr. 2015, 3 pages, ResearchGate, DOI:10.1109/NEBEC.2015.7117097, Retrieved from the Internet: <URL: https://www.researchgate.net/publication/277954299_Computer_Simulation_of_Dental_implant_Treatments>.

(Continued)

*Primary Examiner* — John J Lee
(74) *Attorney, Agent, or Firm* — Elliot J. Shine (57) ABSTRACT

A method, computer system, and a computer program product for simulating dental implants is provided. The present invention may include generating one or more digital twins for a potential dental implant based on a user profile. The present invention may include simulating a performance of each of the one or more digital twins in one or more user modeled environments. The present invention may include ranking the one or more digital twins based on the performance of the potential dental implant in each of the one or more user modeled environments. The present invention may include monitoring a selected dental implant using a corresponding digital twin.

20 Claims, 5 Drawing Sheets

(52) U.S. Cl.
CPC .............. *G06T 2207/20084* (2013.01); *G06T 2207/30036* (2013.01); *G06T 2207/30052* (2013.01)

(56) References Cited

U.S. PATENT DOCUMENTS

| | | |
|---|---|---|
| 10,813,721 B2 | 10/2020 | Sterental |
| 2008/0305452 A1 | 12/2008 | Sterental |
| 2014/0154655 A1* | 6/2014 | Bell ....................... G09B 23/32 434/262 |
| 2018/0153659 A1 | 6/2018 | Fisker |
| 2019/0087544 A1* | 3/2019 | Peterson ................ G16H 50/20 |
| 2021/0107272 A1 | 4/2021 | Fisker |

OTHER PUBLICATIONS

Ma, et al., "Simulation analysis of impact damage to the bone tissue surrounding a dental implant," Scientific Reports, 2020, 11 pages, vol. 10, Article: 6927, Retrieved from the Internet: <URL: https://doi.org/10.1038/s41598-020-63666-5>.

Mell et al., "The NIST Definition of Cloud Computing", National Institute of Standards and Technology, Special Publication 800-145, Sep. 2011, 7 pages.

Surovas, "A digital workflow for modeling of custom dental implants," 3D Printing in Medicine [article], 2019, 11 pages, vol. 5, Issue 9, BMC, Retrieved from the Internet: <URL: https://doi.org/10.1186/s41205-019-0046-y>.

* cited by examiner

DENTAL IMPLANT RECONSTRUCTION AND RESTORATION BASED ON DIGITAL TWIN

BACKGROUND

The present invention relates generally to the field of computing, and more particularly for simulating dental implants.

Dental implant surgery may be a procedure that replaces tooth roots with metal screwlike posts and/or replaces missing teeth with artificial teeth that may function as original teeth. Dental implant surgery may offer an alternative to dentures and/or bridgework that may not work for a patient. How dental implant surgery may be performed may depend on at least a type of implant and/or the condition of a patient's jawbone. Dental implant surgery may require more than one procedure and may require bone of the patient to heal around the implant, which may be a months long process.

Dental implant surgery may require significant due diligence on the part of a surgeon both pre and post-operation. Pre-operation the surgeon may need to assess a variety of factors, including at least implant materials, length and width of an implant, implant position, type of abutment, angle of abutment, tooth conditions, jaw conditions, and/or bone conditions, amongst other determinations. Furthermore, post-operation monitoring the implant as well as patient behavior may be critical to placing a successful implant.

SUMMARY

Embodiments of the present invention disclose a method, computer system, and a computer program product for simulating dental implants. The present invention may include generating one or more digital twins for a potential dental implant based on a user profile. The present invention may include simulating a performance of each of the one or more digital twins in one or more user modeled environments. The present invention may include ranking the one or more digital twins based on the performance of the potential dental implant in each of the one or more user modeled environments. The present invention may include monitoring a selected dental implant using a corresponding digital twin.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for dental implants. As such, the present embodiment has the capacity to improve the technical field of dental implants by simulating dental implant surgery using one or more digital twins. More specifically, the present invention may include generating one or more digital twins for a potential dental implant based on a user profile. The present invention may include simulating a performance of each of the one or more digital twins in one or more user modeled environments. The present invention may include ranking the one or more digital twins based on the performance of the potential dental implant in each of the one or more user modeled environments. The present invention may include monitoring a selected dental implant using a corresponding digital twin.

As described previously, dental implant surgery may be a procedure that replaces tooth roots with metal screwlike posts and/or replaces missing teeth with artificial teeth that may function as the original teeth. Dental implant surgery may offer an alternative to dentures and/or bridgework that may not work for a patient. How dental implant surgery may be performed may depend on at least a type of implant and/or the condition of a patient's jawbone. Dental implant surgery may require more than one procedure and may require bone of the patient to heal around the implant, which may be a several month long process.

Dental implant surgery may require significant due diligence on the part of a surgeon both pre and post-operation. Pre-operation the surgeon may need to determine at least, implant materials, length and width of the implant, implant position, type of abutment, angle of abutment, tooth conditions, jaw conditions, and bone conditions, amongst other determinations. Furthermore, post-operation monitoring the implant as well as patient behavior may be critical to a successful implant.

Therefore, it may be advantageous to, among other things, generate one or more digital twins for a potential dental implant based on a user profile, simulate a performance of each of the one or more digital twins in one or more user modeled environments, rank the one or more digital twins based on the performance of the potential dental implant in each of the one or more user modeled environments, and monitor a selected dental implant using a corresponding digital twin.

According to at least one embodiment, the present invention may improve the operational process of and/or the implant materials used for dental implant surgery by simulating the performance of one or more digital twins in one or more user modeled environments.

According to at least one embodiment, the present invention may improve preventative medicine by utilizing one or more digital twins to simulate the performance of a dental implant surgery.

According to at least one embodiment, the present invention may improve user personalized dental implants by generating 3D printing instructions for one or more components of the dental implant selected by the user.

According to at least one embodiment, the present invention may improve dental implant surgery by simulating at least biocompatibility performance, bone and/or soft tissue cultivation performance, implant side effects, and implant stress performance.

According to at least one embodiment, the present invention may improve user evaluation of unique dental implant options based on at least, simulation data, potential treatment plans, and projected cost.

According to at least one embodiment, the present invention may improve preventative medicine by monitoring the performance of a dental implant using a corresponding digital twin. The digital twin may also be used for one or more life cycle simulations in identifying one or more potential complications associated with a dental implant. Additionally, the digital twin may be used for providing one or more recommendations to a user and/or dental specialist based on the one or more life cycle simulations of the corresponding digital twin.

According to at least one embodiment, the present invention may reduce the side effects experienced by dental implant surgery patients. Side effects of dental implant surgery may include, but are not limited to including, aesthetic complications, peri-implant inflammation, damage to surrounding structures such as teeth or blood vessels, swelling of the gums or face, bruising of the skin or gums, pain at the implant site, prolonged bleeding, health of soft and hard tissue, nerve damage, and/or sinus problems, amongst other side effects.

Figure 1:
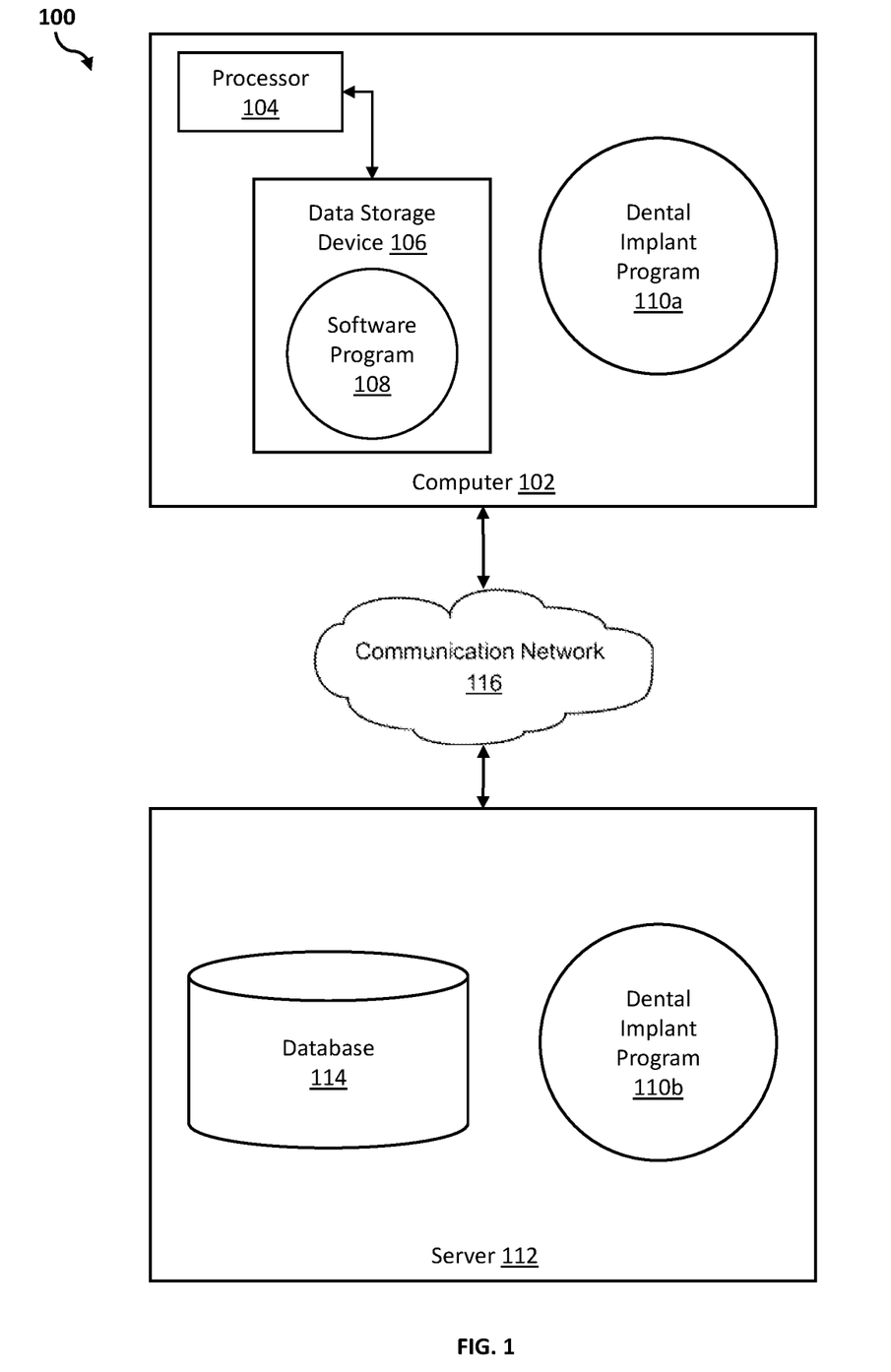
FIG. 1 illustrates a networked computer environment according to at least one embodiment.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a dental impact program 110a. The networked computer environment 100 may also include a server 112 that is enabled to run a dental impact program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the dental impact program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the dental implant program 110a, 110b (respectively) to simulate a plurality of dental implant surgeries utilizing one or more generated digital twins. The dental implant method is explained in more detail below with respect to FIG. 2.

Figure 2:
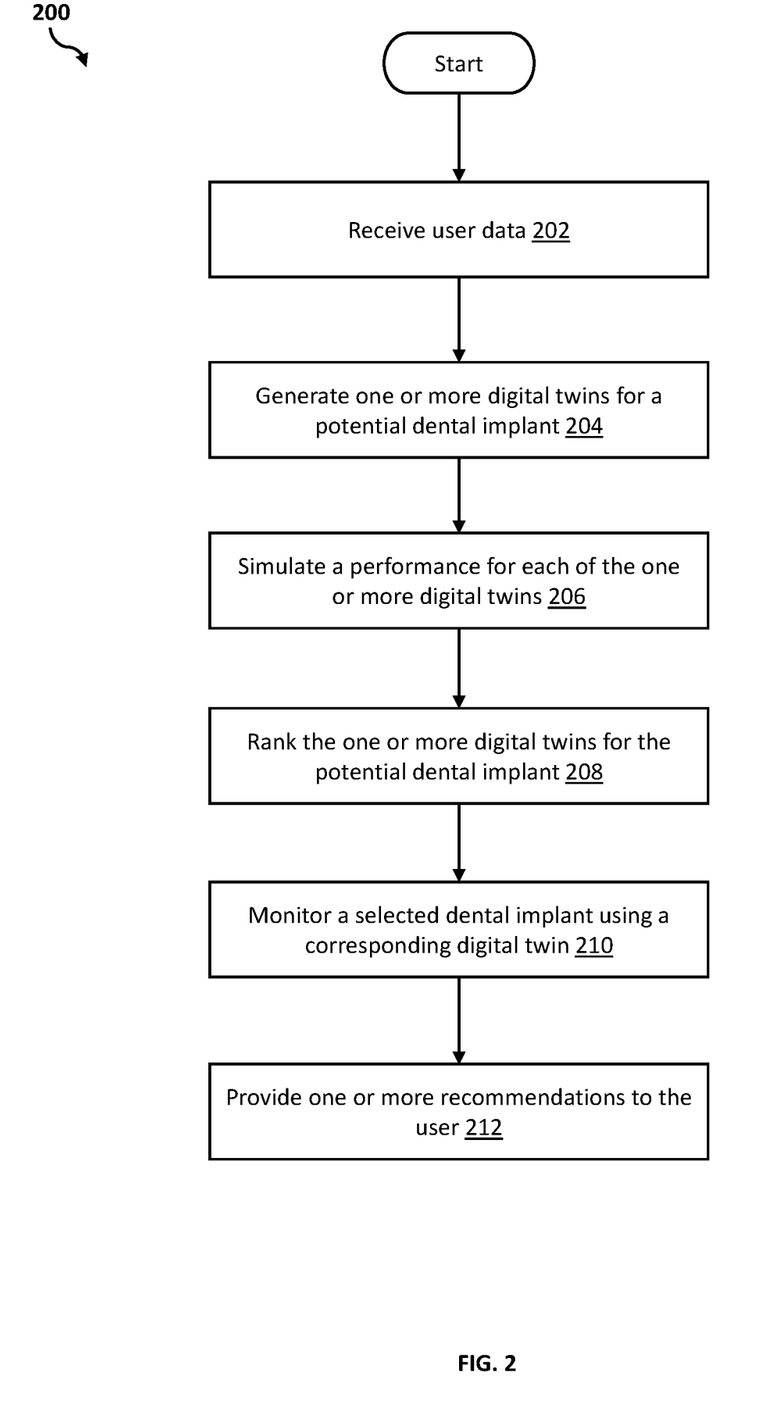
FIG. 2 is an operational flowchart illustrating a process for imaging dental implants according to at least one embodiment.

Referring now to FIG. 2, an operational flowchart illustrating the exemplary dental implant process 200 used by the dental implant program 110a and 110b (hereinafter dental implant program 110) according to at least one embodiment is depicted.

At 202, the dental implant program 110 receives user data. The user data may be for a patient requiring dental implant surgery. User data may include, but is not limited to including, Electronic Dental Records (EDR), Electronic Medical Records (EMR), dental scans, tomographic imaging, radiograph imaging, dental profiling, X-rays, dental impressions, teeth color, pre-existing medical condition(s), bone conditions, bone quality, characteristics of the bone matrix, microarchitecture, bone turnover, accumulation of microdamage, degree of calcification, collagen content, teeth conditions, jaw conditions, IoT (Internet of Things) data, consumption data, amongst other user data relevant to dental implant surgery. All user data received by the dental implant program 110 shall not be construed as to violate or encourage the violation of any local, state, federal, or international law with respect to privacy protection. The dental implant program 110 may receive consent from the user and/or a dental specialist prior to receiving the user data.

As will be explained in more detail below, consumption data may be gathered for the user pre-operation and/or post-operation. Consumption data may include, but is not limited to including, food intake, saliva pH (power of hydrogen), quantity of acidic beverages consumed, quantity of acidic foods consumed, and/or blood alcohol levels, amongst other consumption data. Consumption data may be received based on at least, one or more of, user input, IoT device tracking, a tele-dentistry appointment, and/or a consultation with a periodontist, oral surgeon, dentist, or other dental specialist, amongst other methods. The consumption data received from IoT device tracking may be received in real time by the dental implant program 110. The dental implant program 110 may further require periodic consent with respect to any additional user data received from the user through at least user input and/or IoT devices. The dental implant program 110 may only receive user data relevant to dental implant surgery. An example of user inputted consumption data may be a user's tracked diet in a mobile application. An example of receiving consumption data through IoT device tracking may include, but is not limited to including, receiving data from one or more, smart toothbrushes, IoT diet wearables, and/or smart teeth. A smart toothbrush may be embedded with technologies such as cameras, and/or pressure sensors, amongst other technologies. Smart teeth may involve the utilization of a microchip either implanted in a tooth or mounted to a tooth with the ability to track user consumption.

The dental implant program 110 may utilize the user data in generating a user profile (e.g., a profile which may be specific to a user, also referred to as a patient, where the data utilized in generating and/or updating the user profile is the patient's data relevant to dental implant surgery). The dental implant program 110 may store the user profile in a knowledge corpus (e.g., database 114). The knowledge corpus (e.g., database 114) may store a plurality of user profiles (e.g., plurality of profiles each specific to a unique user), a sub-set of which may be utilized by the dental implant program 110. As will be explained in more detail below, the user data and user profile may be utilized by the dental implant program 110 in generating one or more digital twins for a potential dental implant placement based on one or more similar user profiles (e.g., one or more other user profiles with similar data relevant to dental implant surgery).

At 204, the dental implant program 110 generates one or more digital twins for a potential dental implant. A digital twin may be a virtual representation of an object or system that spans the object or system's lifecycle, may be updated using real-time data, and may utilize at least, simulation, machine learning, and/or reasoning in aiding informed decision making. The dental implant program 110 may generate the one or more digital twins based on at least the user data and/or user profile and the sub-set of one or more similar user profiles stored in the knowledge corpus (e.g., database 114). The dental implant program 110 may also generate one or more digital twins based on specifications received from a dental specialist.

The dental implant program 110 may generate the one or more digital twins for the potential dental implant based on at least, one or more of, a virtual representation of the user, an operational process, and/or implant properties. The virtual representation of the user may include at least the fourteen facial bones, soft tissue, and teeth of the user. The dental implant program 110 may generate the virtual representation based on at least the user data received. The virtual representation may also incorporate user data such as, but not limited to, jawbone conditions and bone mineral density. As will be explained in more detail below with respect to step 210, the dental implant program 110 may update the user data incorporated into the virtual representation of the user. Each of the one or more digital twins generated by the dental implant program 110 may be unique with respect to at least, the operational process and/or the implant properties.

Dental implant surgery may include five main steps. First, the removal of one or more teeth. Second, insertion of a dental implant. Third, osseointegration of the dental implant. Fourth, abutment placement atop the dental implant. Fifth, the addition of a crown or an artificial tooth. The operational process with respect to each step may vary considerably. The operational process may vary with respect to at least, inserting the dental implant into the jawbone or under the gumline, implant loading types, healing periods, osseointegration time, sinus augmentation, bone level tapering, amongst other operational processes. The implant properties may also vary considerably. The implant properties may vary with respect to at least, materials of an artificial tooth and/or crown, abutment materials, implant materials, width of implant, length of implant, abutment angles, amongst other implant properties. Materials utilized in dental implant surgery may include, but are not limited to including, one or more of, Niobium, Zirconia, Titanium, porcelain, steel, amongst other materials currently utilized and/or hereinafter utilized.

The dental implant program 110 may utilize the one or more similar user profiles in determining different combinations of operational processes and/or implant properties that either resulted in a successful dental implant surgery and/or resulted in one or more complications in the dental implant surgery.

For example, the dental impact program 110 receives user data for User 1. Based on the user data from User 1 the dental impact program 110 may generate User Profile 1 and may store User Profile 1 in the knowledge corpus (e.g., database 114). Based on User Profile 1 the dental implant program may identify four similar user profiles within the knowledge corpus. Of the four similar user profiles three reported a dental implant surgery and one reported an unsuccessful dental implant surgery. The dental impact program 110 may generate five unique combinations of operational processes and/or implant properties based on the three successful surgeries and the one unsuccessful surgery. The dental impact program 110 may utilize the five unique combinations of operational processes and/or implant properties to generate five digital twins, Digital Twin 1, Digital Twin 2, Digital Twin 3, Digital Twin 4, and Digital Twin 5. Additionally, the dental impact program 110 may receive specifications from the oral surgeon scheduled to perform the dental implant surgery for User 1. The specifications from the oral surgeon may include both the operational process and implant properties the oral surgeon had planned to utilize in the surgery based on the surgeon's examination and/or user data available to the surgeon. The dental impact program 110 may generate Digital Twin 6 based on the specifications received from the oral surgeon. Digital Twin 1 may be for a titanium implant inserted into the jawbone of User 1, a 12 week osseointegration period, a 15 degree titanium angular abutment, and porcelain crown. Digital Twin 2 may be for a titanium, niobium, and zirconia implant inserted into the jawbone of User 1, a 12 week osseointegration period, a 15 degree titanium angular abutment, and porcelain crown. Digital Twin 3 may be for a titanium implant inserted under the gumline of User 1, a 16 week osseointegration period, a 25 degree titanium angular abutment, and porcelain crown. Digital Twin 4 may be for a titanium, niobium, and zirconia implant inserted under the gumline of User 1, a 14 week osseointegration period, a 35 degree titanium angular abutment, and zirconium crown. Digital Twin 5 may be for a titanium implant inserted into the jawbone of User 1, a 12 week osseointegration period, a 15 degree titanium angular abutment, porcelain crown, and sinus augmentation. Digital Twin 6 may be for a titanium implant inserted into the jawbone of User 1, a 16 week osseointegration period, no angular abutment, and porcelain crown. As will be explained in more detail below, the dental implant program 110 may simulate the performance of each of the six digital twins in a user modeled environment. It should be noted that any specific material (e.g., titanium) or process (e.g., osseointegration) may be merely exemplary with the present invention not being limited to either presently or future developed materials and/or processes.

At 206, the dental implant program 110 simulates the performance for each of the one or more digital twins. The dental implant program 110 may simulate the performance for each of the one or more digital twins in one or more user modeled environments. The dental implant program 110 may utilize one or more machine learning models in simulating the performance of the one or more digital twins in the one or more user modeled environments. The one or more machine learning models may include, but are not limited to including, Convolutional Neural Networks (CNNs), Artificial Neural Networks (ANNs), Support Vector Machine (SVM), K-Nearest Neighbors (KNN), Naïve Bayes, and/or a hybrid model. The hybrid model may be trained to combine the predictions of two or more machine learning models.

The dental implant program 110 may generate the one or more user modeled environments using, at least one or more of, the user profile, user data, and/or consumption data. The dental implant program 110 may adjust, at least one or more of, the user profile user data, and/or consumption data. The dental implant program 110 may generate a user modeled environment for each adjustment, wherein each adjustment may deviate from at least one or more of, the user profile, user data, and/or consumption data, such that each of the one or more user modeled environments may allow the dental implant program 110 to account for at least errors and/or lack of data received from the user. As will be explained in more detail below, the dental implant program 110 may data based on the quantity and/or quality of the data to account for at least errors and/or deviations. For example, User 1 may have provided 3 weeks of consumption data using a diet tracking mobile application and User 2 may have provided 3 months of consumption data from a smart toothbrush and IoT diet wearable. The dental implant program 110 may adjust the user modeled environment of User 1, 20 times to account for a likelihood User 1 deviates from the consumption data provided. On the other hand, the dental implant program 110 may adjust the user modeled environment of User 2, 3 times to account the likelihood User 2 deviates from the consumption data provided. In this example, the diet tracking mobile application used by User 1 may be considered lower quality data as compared to the higher quality data provided from User 2 from the smart toothbrush and IoT diet wearable. Additionally, the 3 weeks of consumption data provided by User 1 may be considered a lower quantity of data compared to the 3 months of consumption data provided by User 2. The number of user modeled environments may impact a confidence score of the simulated performance for each of the one or more digital twins. In the above example, if the dental impact program 110 generated three digital twins for User 1, the dental impact program 110 would simulate each of the three digital twins 20 times, for a total of 60 digital twin simulations. If the dental impact program 110 generated ten digital twins for User 2, the dental impact program 110 would simulate each of the ten digital twins 3 times, for a total of 30 digital twin simulations.

Simulating the performance for each of the one or more digital twins may include, but is not limited to including, implant stress performance, implant biocompatibility performance, bone and/or soft tissue cultivation performance, implant side effects, amongst other performance indicators.

The dental implant program 110 may simulate implant stress performance by monitoring at least, tensile stress, vertical stress, and/or angular stress, which may be simulated for each of the one or more digital twins in the one or more user modeled environments. For example, the dental implant program 110 may have received several weeks of consumption data from User 1 from a diet tracking mobile application. The dental implant program 110 may simulate the performance of each of the one or more digital twins based on the consumption data of User 1 and how each model performed with respect to implant stress. In this example, a digital twin which chipped, fractured, or loosened may be weighted negatively with respect to implant stress performance.

The dental implant program 110 may simulate implant biocompatibility performance based on at least, biological microbial interactions, toxicity generation, and/or corrosive monitoring, amongst other factors. The dental implant program 110 may simulate the implant biocompatibility performance over a lifecycle span of each of the one or more digital twins. For example, User 1 may require a lifecycle of 50 years for the dental implant and User 2 may require a lifecycle of 20 years for the dental implant. In both the User 1 and User 2 simulations the digital twins with a titanium implant corroded after 40 years and the digital twins with a zirconia implant showed no signs of corrosion but required replacement after 60 years. For User 1 the titanium implant may be weighted slightly negatively, and the zirconia implant may be weighted positively with respect to biocompatibility performance. For User 2 both the titanium implant and the zirconia implant may be weighted positively.

The dental implant program 110 may simulate bone and/or soft tissue cultivation performance for each of the one or more digital twins in the one or more user modeled environments by monitoring at least bone turnover markers (BTMs). BTMs may include, but are not limited to including, bone mineral density, soft bone tissue, bone width, and cortical-trabecular bone thickness. BTMs levels may vary significantly based on preanalytical factors and/or comorbid clinical conditions. Additionally, BTMs may respond rapidly to changes in bone physiology.

In an embodiment, the dental implant program 110 may also include a potential treatment plan for each of the one or more digital twins based on at least the simulated resulting side effects. As will be explained in more detail below, the potential treatment plan for each of the one or more digital twins may be included in the simulation data provided to the user.

At 208, the dental implant program 110 ranks the one or more digital twins. The dental implant program 110 may rank the one or more digital twins based on the simulation performance, wherein each of the performance of each of the one or more digital twins may represent the performance of a potential dental implant in each of the one or more user modeled environments. The ranking of the one or more digital twins may include a recommended dental implant for the user. The recommended dental implant for the user may be a highest ranked digital twin.

The dental implant program 110 may include simulation data for each of the one or more digital twins based on the simulation performance of the digital twin in the one or more user modeled environments. The simulation data for each of the one or more digital twins may include at least, implant stress performance data, implant biocompatibility performance data, and soft tissue cultivation data, implant side effects data, when an implant failed, why an implant failed, complications with each dental implant, and/or the effect of consumption data on the performance simulation for each digital twin, amongst other data. The dental implant program 110 may also include a result probability and/or confidence score with respect to the simulation data. The result probability and/or confidence score may be represented using a percentage, fraction, term (e.g., high, medium, low), or other representation.

The dental implant program 110 may also provide a potential treatment plan for each of the one or more digital twins. The treatment plan may include, but is not limited to including, oral hygiene recommendations, dietary restrictions, a timeline for recommended follow up appointments with the dental specialist, and/or medications, amongst other potential treatments.

The dental implant program 110 may also include a projected cost for a dental implant surgery with respect to each of the one or more digital twins. The dental implant program 110 may determine the projected cost based on at least the implant materials and/or the user's insurance provider, only as provided by the user. A projected cost may be dynamic and/or modifiable based on a change in a user's insurance provider and/or plan, a change in cost of implant materials, and/or a change in physician. All insurance provider data received by the dental implant program 110 shall not be construed as to violate or encourage the violation of any local, state, federal, or international law with respect to privacy protection. The dental implant program 110 may receive consent from the user prior to determining the projected cost for each of the one or more digital twins.

For example, the dental implant program 110 may generate two digital twins for User 1 based on five similar patient profiles, Digital Twin 1 and Digital Twin 2. The dental implant program 110 may generate a third digital twin based on specifications received from User 1's dental specialist, Digital Twin 3. The dental implant program 110 may have received a limited amount of consumption data for User 1, requiring the dental implant program 110 to simulate the performance of each digital twin in 20 user modeled environments. The dental implant program 110 may have ranked Digital Twin 3 the highest, Digital Twin 2 second, and Digital Twin 1 the lowest. Digital Twin 3 may have had no major complications during any of the performance simulations, a 24 week osseointegration period, but corroded in under 25 years in all simulations. Accordingly, the dental implant program 110 may have determined a high result probability of no major complications for Digital Twin 3 with a high confidence score. Digital Twin 2 may have had two major complications including an implant failure, a 12 week osseointegration period, and corroded after 75 years in 18 of the 20 simulations. Accordingly, the dental implant program 110 may have determined a high result probability of major complications. Digital Twin 1 may have had six major complications during the 20 simulation performances, implant side effects in four simulation performances, a 24 week osseointegration period, and corroded after 15 years. Accordingly, the dental implant program 110 may have determined a high result probability of major complications. In this example, User 1 and the dental specialist may review the rankings of the three digital twins as well as the simulation data and notice the two user modeled environments that resulted in major complications for Digital Twin 2 are unrepresentative of User 1's consumption habits. User 1 may have stopped smoking, drinking alcohol, or the consumption data was unrepresentative of User 1's dietary habits and the potential treatment plan's dietary restrictions for Digital Twin 2 are easily achievable. Additionally, the potential treatment plan's dietary restrictions for Digital Twin 2, the osseointegration period and the projected cost are more favorable to User 1 as compared to Digital Twin 3. Accordingly, User 1 and the dental specialist may select Digital Twin 2. User 1 and the dental specialist may also provide updated consumption data to the dental implant program 110 to re-run the simulation performance of the three digital twins.

In an embodiment, the dental implant program 110 may request additional consumption data of the user based on at least, the simulation performance results, a threshold of user modeled environments being exceeded, one or more confidence scores below a threshold confidence score, amongst other reasons. The dental implant program 110 may request the additional consumption data by at least displaying a message and/or notification with the rankings of the one or more digital twins.

In an embodiment, the dental implant program 110 may generate 3D printing instructions for one or more components of the dental implant selected by the user. For example, the user may select a dental implant based on the ranking of the one or more digital twins, the corresponding dental implant for Dental Implant 2 may be Digital Twin 2. The crown virtually represented in Digital Twin 2 may be a ceramic with infused anti-microbial properties in a shade that matches the user's natural tooth color. Accordingly, the dental implant program 110 may generate 3D printing instructions for the ceramic crown with infused anti-microbial properties in the shade that matches the user's natural tooth color.

In an embodiment, the dental implant program 110 may enable a dental specialist to adjust at least the operational processes and/or implant properties of the one or more digital twins and simulate the performance of the one or more adjusted digital twins for the user. The dental implant program 110 may retrain the machine learning model based on the simulated performance of the one or more adjusted digital twins for the user. For example, if Digital Twin 1 is the highest ranked digital twin and then the dental specialist adjusts an implant property and the adjusted digital twin ranks higher than Digital Twin 1, the dental implant program may retrain the machine learning model.

At 210, the dental implant program 110 monitors a selected dental implant. The dental implant program 110 may monitor the dental implant (e.g., selected dental implant) through the one or more steps of dental implant surgery and post-operation. The dental implant program 110 may monitor the dental implant (e.g., selected dental implant) using a corresponding digital twin, the corresponding digital twin being the digital twin of the dental implant selected by the user from the ranking of the one or more digital twins. The dental implant program 110 may monitor the dental implant (e.g., selected dental implant) using new data, such as, but not limited to, surgical procedure data, additional consumption data, updated user data, and/or additional user data, amongst other new data. The dental implant program 110 may also utilize the new data to update the user profile stored in the knowledge corpus (e.g., database 114). As detailed above with respect to step 204, the dental implant program 110 may utilize the user profile (e.g., patient profile) in generating digital twins for one or more similar users.

The dental implant program 110 may monitor the dental implant (e.g., selected dental implant) surgical procedure using one or more hand and/or tool motion tracking techniques, such as, but not limited to, Optical Tracking, Electromagnetic Tracking, amongst other motion tracking systems. Optical Tracking Systems may consist of a receiver until including two or more cameras and a set of special markers attached to the object. Electromagnetic Tracking Systems may consist of three components, a field generator, sensor unit, and central control unit. The dental implant program 110 may utilize the one or more hand and/or tool motion tracking techniques in monitoring at least, the removal of one or more teeth, insertion of the dental implant, abutment placement atop the dental implant, and the addition of an artificial tooth or crown. The dental implant program 110 may utilize the data received from the dental implant surgical procedure to update the corresponding digital twin. The dental implant program 110 may utilize surgical procedure data such as, but not limited to, insertion torque, probing torque, heat production, bone socket diameter, bone socket tapering angles, amongst other data, captured images of the dental implant (e.g., selected dental implant, in updating the corresponding digital twin.

The dental implant program 110 may utilize at least, additional consumption data, updated user data, and/or additional user data, such as data received from follow up appointments, to monitor the dental implant and/or update the corresponding digital twin throughout osseointegration and/or post-operation.

The dental implant program 110 may utilize the one or more machine learning models to update the corresponding digital twin using the new data. The dental implant program 110 may run a simultaneous simulation of the corresponding digital twin to monitor the dental implant (e.g., selected dental implant). The dental implant program 110 may retrain the one or more machine learning models based on a comparison of the dental implant and the corresponding digital twin. For example, the dental implant program 110 may receive the surgical procedure data, updated Electronic Dental Records, new radiograph imaging, amongst other new data, following the insertion of the dental implant. At this point the corresponding digital twin is a virtual representation of the dental implant (e.g., selected dental implant). The osseointegration period between the insertion of the dental implant and the abutment placement atop the dental implant may be 14 weeks with a scheduled follow up appointment mid-way through at 7 weeks. Between the insertion of the dental implant and the follow up appointment the dental implant program may receive additional consumption data from one or more user IoT devices. The dental implant program 110 may run the simultaneous simulation of the corresponding digital twin for 7 weeks using the additional consumption data. At the 7-week follow up appointment the dental implant program 110 may receive new data detailing the progress, state, and other details of the dental implant, which may be utilized in determining the actual performance of the dental implant implanted in the user during that 7-week period. The dental implant program 110 may compare the corresponding digital twin with the dental implant (e.g., selected dental implant) based on the new data received. The dental implant program 110 may store the differences in the knowledge corpus (e.g., database 114) and utilize the differences in retraining the one or more machine learning models.

The differences may be stored in the knowledge corpus (e.g., database 114) and utilized in retraining the one or more machine learning models to improve performance simulations of future digital twins. In the above example, based on the consumption data received from the user leading up to the 7-week follow up appointment the dental implant program 110 simulated the performance of the dental implant using the consumption data. The new data received at the 7-week follow up appointment shows the dental implant (e.g., selected dental implant) did not perform as expected based on the corresponding digital twin in the 7 intervening weeks. The dental implant program 110 may compare the corresponding digital twin and the dental implant (e.g., selected dental implant) and store the differences in the knowledge corpus (e.g., database 114). User 2 may be a user with a similar user profile in day 1 of the osseointegration period. The dental implant program 110 may receive very similar consumption data from User 2 during User 2's osseointegration period. The one or more machine learning models, having been retrained using the differences stored in the knowledge corpus (e.g., database 114), may simulate the performance of User 2's dental implant (e.g., the dental implant selected by User 2) using User 2's corresponding digital twin. At User 2's 7-week follow up appointment the new data may show that User 2's corresponding digital twin accurately reflects the dental implant (e.g., the dental implant selected by User 2). The dental implant program 110 may store the small differences between User 2's corresponding digital twin and User 2's dental implant (e.g., the dental implant selected by User 2) in the knowledge corpus (e.g., database 114). The dental implant program 110 may utilize the simulations to identify relationships between consumption data and user profiles to provide personalized recommendations to the user.

The dental implant program 110 may also run one or more life cycle simulations of the corresponding digital twin each time new data is received using the one or more machine learning models. The one or more life cycle simulations may be utilized in identify potential complications in the dental implant (e.g., selected dental implant). The dental implant program 110 may utilize the one or more life cycle simulations in providing one or more recommendations to the user and/or dental specialist.

In an embodiment, the dental implant program 110 may generate a smart contract between a user and an insurance company. A smart contract may be a program stored on a blockchain the executes upon the fulfillment of predetermined conditions. For example, the dental implant program 110 may attach incentives to the treatment plan of the user in exchange for reduction of liability if the user's implant fails following a violation of the treatment plan. The smart contract may be stored on the blockchain and executed based on consumption data received by the dental implant program 110 from one or more agreed IoT devices.

At 212, the dental implant program 110 provides one or more recommendations. The dental implant program 110 may provide the one or more recommendations to the user and/or to a dental specialist (e.g., a dentist, a dental hygienist, among other dental specialists). The dental implant program 110 may provide the recommendations based on any new data collected as a result of any life cycle simulations of the corresponding digital twin. The new data may reveal issues with the dental implant and/or the user's dental hygiene for which there may be a solution and/or a recommendation may be provided.

The recommendations may include, but are not limited to including, oral hygiene recommendations, such as an interdental brush, recommended dietary adjustments, such as food and/or drink substitutions based on consumption data, chewing recommendations, scheduling a follow up appointment, amongst other recommendations. In an embodiment the dental implant program 110 may schedule appointments automatically. The dental implant program 110 may utilize calendaring data of the dental specialist and request confirmation from the user.

The dental implant program 110 may request the user upload images of the dental implant (e.g., selected dental implant) prior to providing the recommendations. The dental implant program 110 may analyze the one or more uploaded images and compare with the corresponding digital twin. The dental implant program 110 may utilize the images of the dental implant in determining an accuracy of the life cycle simulations of the corresponding digital twin.

For example, the dental implant program 110 may run one or more life cycle simulations of the corresponding digital twin based on new data received. In one or more of the life cycle simulations the corresponding digital twin may fail prior to the user's next scheduled appointment. The dental implant program 110 may request the user upload images of the dental implant to determine if the one or more life cycle simulations are accurate based on the current state of the dental implant. The user may upload the images and the dental implant program 110 may compare those images to the dental implant and determine any differences between the corresponding digital twin and the dental implant. If the corresponding digital twin is an accurate representation of the dental implant the dental implant program 110 may determine the one or more life cycle simulations are accurate. Accordingly, the dental implant program 110 may recommend the user schedule a follow up appointment with the dental specialist prior to the simulated dental implant failure. Alternatively, the corresponding digital twin may be inaccurate. The user may have for example forgot to input consumption data and/or the data received from an IoT device may have been inaccurate. Here, the dental implant program 110 may utilize the uploaded images to update the corresponding digital twin to accurately reflect the dental implant. The dental implant program 110 may then run one or more life cycle simulations of the updated corresponding digital twin and determine that the dental implant does not fail in any life cycle simulations prior to the user's next scheduled appointment. The dental implant program 110 may not recommend scheduling a follow up appointment with the dental specialist prior to the next scheduled appointment. The dental implant program 110 may still provide other recommendations such as oral hygiene recommendations.

It may be appreciated that FIG. 2 provides only an illustration of one embodiment and do not imply any limitations with regard to how different embodiments may be implemented. Many modifications to the depicted embodiment(s) may be made based on design and implementation requirements.

Figure 3:
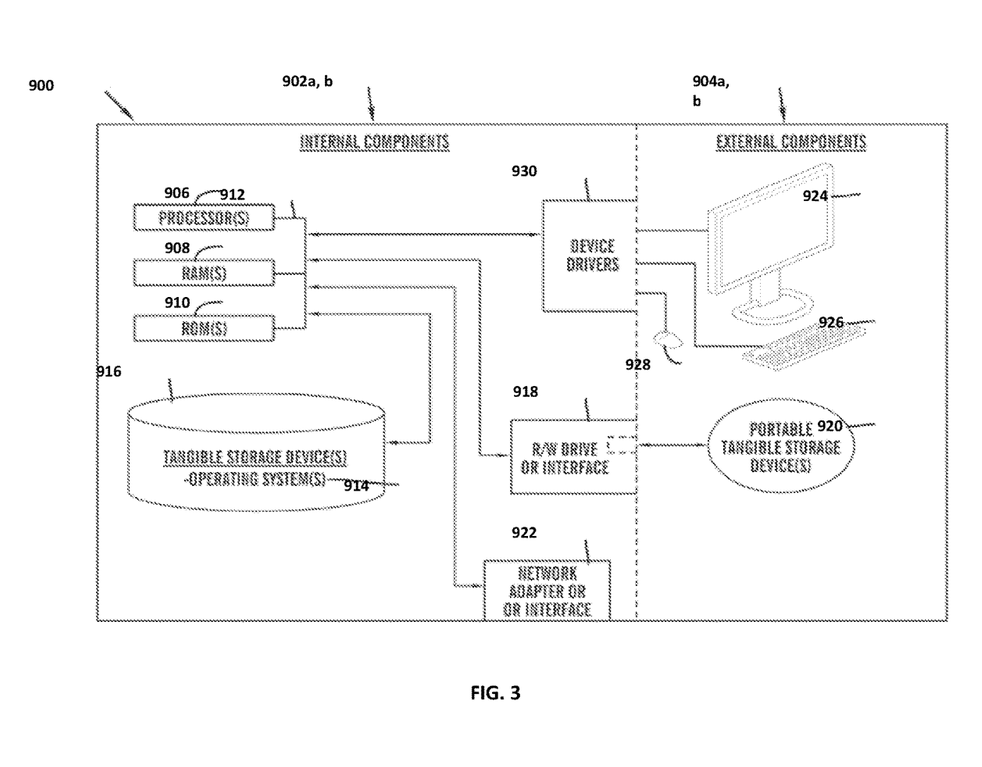
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 *a, b* and external components 904 *a, b* illustrated in FIG. 3. Each of the sets of internal components 902 *a, b* includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the dental implant program 110*a* in client computer 102, and the dental implant program 110*b* in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 *a, b* also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the dental implant program 110*a* and 110*b* can be stored on one or more of the respective portable computer-readable tangible storage devices 920, read via the respective R/W drive or interface 918 and loaded into the respective hard drive 916.

Each set of internal components 902 *a, b* may also include network adapters (or switch port cards) or interfaces 922 such as a TCP/IP adapter cards, wireless wi-fi interface cards, or 3G or 4G wireless interface cards or other wired or wireless communication links. The software program 108 and the dental implant program 110*a* in client computer 102 and the dental implant program 110*b* in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the dental implant program 110*a* in client computer 102 and the dental implant program 110*b* in network server computer 112 are loaded into the respective hard drive 916. The network may comprise copper wires, optical fibers, wireless transmission, routers, firewalls, switches, gateway computers and/or edge servers.

Each of the sets of external components 904 *a, b* can include a computer display monitor 924, a keyboard 926, and a computer mouse 928. External components 904 *a, b* can also include touch screens, virtual keyboards, touch pads, pointing devices, and other human interface devices. Each of the sets of internal components 902 *a, b* also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
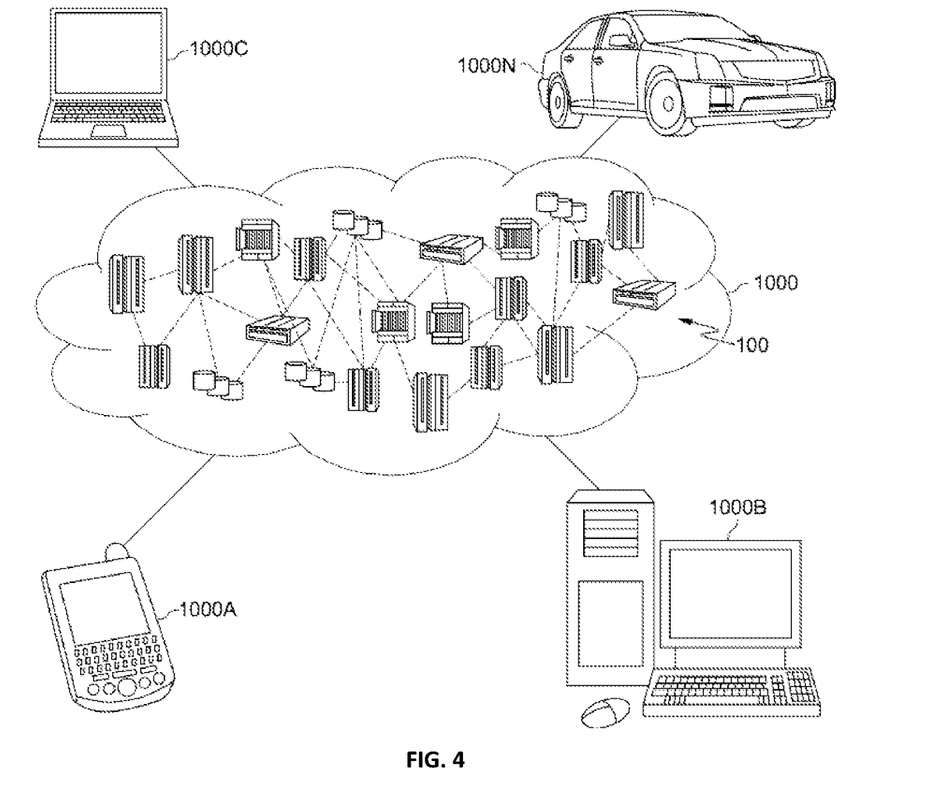
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
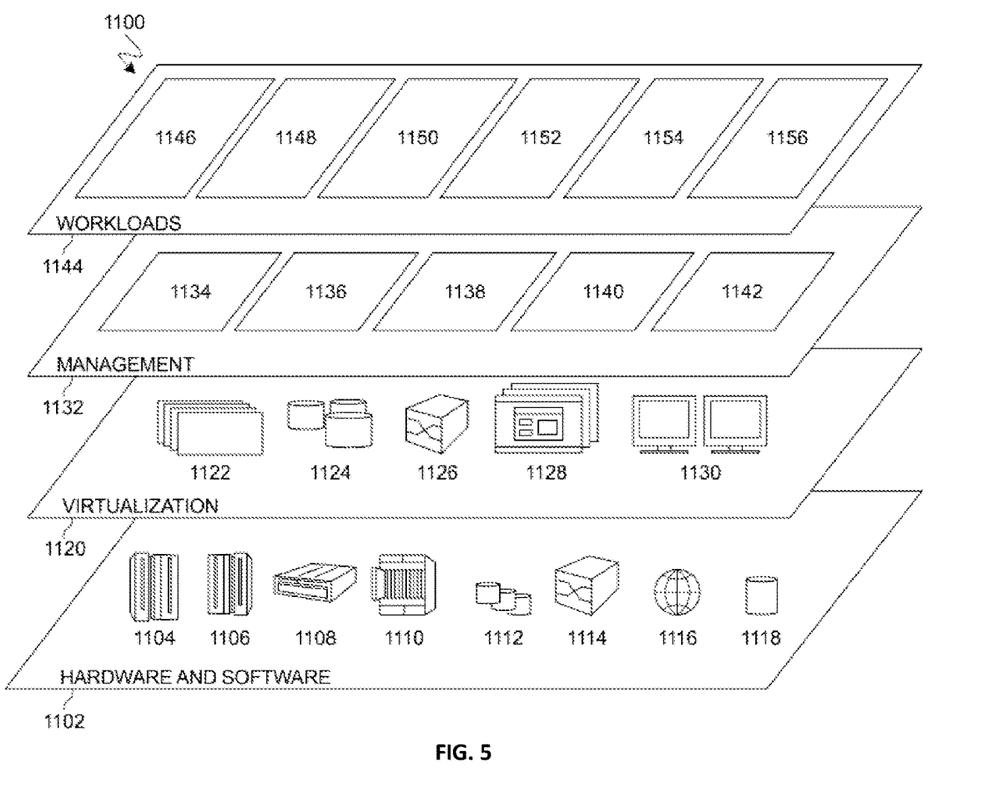
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and dental implant 1156. A dental implant program 110*a*, 110*b* provides a way to simulate dental implant surgery utilizing one or more digital twins.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

The present disclosure shall not be construed as to violate or encourage the violation of any local, state, federal, or international law with respect to privacy protection.

What is claimed is:

1. A method for simulating dental implants, the method comprising:
   generating one or more digital twins for a potential dental implant based on a user profile;
   simulating a performance of each of the one or more digital twins in one or more user modeled environments;
   ranking the one or more digital twins based on the performance of the potential dental implant in each of the one or more user modeled environments; and
   monitoring a selected dental implant using a corresponding digital twin as new data is received.

2. The method of claim 1, wherein each of the one or more digital twins is unique with respect to operational process or implant properties.

3. The method of claim 1, wherein the corresponding digital twin is a virtual representation of the selected dental implant, wherein the selected dental implant is determined based on the ranking of the one or more digital twins.

4. The method of claim 1, wherein monitoring the dental implant further comprises:
   running a simultaneous simulation of the corresponding digital twin using one or more machine learning models as the new data is received; and
   identifying one or more differences between the selected dental implant and the corresponding digital twin based on a comparison.

5. The method of claim 4, further comprising:
   retraining the one or more machine learning models based on the one or more differences between the selected dental implant and the corresponding digital twin.

6. The method of claim 1, further comprising:
   running one or more life cycle simulations of the corresponding digital twin each time the new data is received; and
   providing one or more recommendations to a user based on the one or more life cycle simulations of the corresponding digital twin.

7. The method of claim 6, wherein the new data is consumption data received in real time from one or more IoT devices.

8. A computer system for simulating dental implants, comprising:
   one or more processors, one or more computer-readable memories, one or more non-transitory tangible computer-readable tangible storage medium, and program instructions stored on at least one of the one or more non-transitory tangible storage medium for execution by at least one of the one or more processors via at least one of the one or more memories, wherein the computer system is capable of performing a method comprising:
   generating one or more digital twins for a potential dental implant based on a user profile;
   simulating a performance of each of the one or more digital twins in one or more user modeled environments;
   ranking the one or more digital twins based on the performance of the potential dental implant in each of the one or more user modeled environments; and
   monitoring a selected dental implant using a corresponding digital twin as new data is received.

9. The computer system of claim 8, wherein each of the one or more digital twins is unique with respect to at least operational process or implant properties.

10. The computer system of claim 8, wherein the corresponding digital twin is a virtual representation of the selected dental implant, wherein the selected dental implant is determined based on the ranking of the one or more digital twins.

11. The computer system of claim 8, wherein monitoring the dental implant further comprises:
    running a simultaneous simulation of the corresponding digital twin using one or more machine learning models as the new data is received; and
    identifying one or more differences between the selected dental implant and the corresponding digital twin based on a comparison.

12. The computer system of claim 11, further comprising:
    retraining the one or more machine learning models based on the one or more differences between the selected dental implant and the corresponding digital twin.

13. The computer system of claim 8, further comprising:
    running one or more life cycle simulations of the corresponding digital twin each time the new data is received; and
    providing one or more recommendations to a user based on the one or more life cycle simulations of the corresponding digital twin.

14. The computer system of claim 13, wherein the new data is consumption data received in real time from one or more IoT devices.

15. A non-transitory computer program product for simulating dental implants, comprising:
one or more non-transitory computer-readable storage media and program instructions stored on at least one of the one or more tangible storage media, the program instructions executable by a processor to cause the processor to perform a method comprising:
generating one or more digital twins for a potential dental implant based on a user profile;
simulating a performance of each of the one or more digital twins in one or more user modeled environments;
ranking the one or more digital twins based on the performance of the potential dental implant in each of the one or more user modeled environments; and
monitoring a selected dental implant using a corresponding digital twin as new data is received.

16. The computer program product of claim 15, wherein each of the one or more digital twins is unique with respect to at least operational process or implant properties.

17. The computer program product of claim 15, wherein the corresponding digital twin is a virtual representation of the selected dental implant, wherein the selected dental implant is determined based on the ranking of the one or more digital twins.

18. The computer program product of claim 15, wherein monitoring the dental implant further comprises:
running a simultaneous simulation of the corresponding digital twin using one or more machine learning models as the new data is received; and
identifying one or more differences between the selected dental implant and the corresponding digital twin based on a comparison.

19. The computer program product of claim 18, further comprising:
retraining the one or more machine learning models based on the one or more differences between the selected dental implant and the corresponding digital twin.

20. The computer program product of claim 15, further comprising:
running one or more life cycle simulations of the corresponding digital twin each time the new data is received; and
providing one or more recommendations to a user based on the one or more life cycle simulations of the corresponding digital twin.

* * * * *